United States Patent
Morales Alvarez (10) Patent No.: US 10,588,720 B2
(45) Date of Patent: Mar. 17, 2020

(54) IMPLANT-SUPPORTED DENTAL PROSTHESIS, REMOVAL DEVICE FOR AUTOMATICALLY REMOVING THE PROSTHESIS, ATTACHMENT PIECE FOR ATTACHING THE PROSTHESIS TO IMPLANTS AND IMPLANT SPLINTING BAR FOR ATTACHING THE PROSTHESIS TO IMPLANTS

(71) Applicant: Jose Carlos Morales Alvarez, Cartagena (ES)

(72) Inventor: Jose Carlos Morales Alvarez, Cartagena (ES)

(*) Notice: Subject to any disclaimer, the term of this patent is extended or adjusted under 35 U.S.C. 154(b) by 198 days.

(21) Appl. No.: 15/575,061

(22) PCT Filed: May 19, 2016

(86) PCT No.: PCT/ES2016/070378
§ 371 (c)(1),
(2) Date: Nov. 17, 2017

(87) PCT Pub. No.: WO2016/185076
PCT Pub. Date: Nov. 24, 2016

(65) Prior Publication Data
US 2018/0140388 A1 May 24, 2018

(30) Foreign Application Priority Data
May 20, 2015 (ES) .................................. 201530692

(51) Int. Cl.
*A61C 8/00* (2006.01)
*A61C 13/271* (2006.01)
(Continued)

(52) U.S. Cl.
CPC .............. *A61C 8/005* (2013.01); *A61C 3/00* (2013.01); *A61C 8/0048* (2013.01); *A61C 13/08* (2013.01);
(Continued)

(58) Field of Classification Search
CPC ..... A61C 8/0089; A61C 8/005; A61C 8/0095; A61C 8/0048; A61C 8/0009;
(Continued)

(56) References Cited

U.S. PATENT DOCUMENTS 2,483,353 A * 9/1949 Seveilhac ............ A61C 13/225
433/178
2,572,714 A * 10/1951 Funderburg, Jr. ..... A61C 13/26
292/164
(Continued)

FOREIGN PATENT DOCUMENTS

WO 2014/081843 A1 5/2014

OTHER PUBLICATIONS

"Definition of pincer", Jul. 3, 2019, Merriam-Webster, https://www.merriam-webster.com/dictionary/pincer (Year: 2019).*
(Continued)

*Primary Examiner* — Sean M Michalski
*Assistant Examiner* — Shannel N Wright
(74) *Attorney, Agent, or Firm* — Collard & Roe, P.C.

(57) ABSTRACT

An implant-supported dental prosthesis, removal device for automatically removing the prosthesis, attachment piece for attaching the prosthesis to implants and an attachment bar for attaching the prosthesis to implants. The prosthesis comprises a compartment with a spacing member that can be actuated through a side opening by means of the device, for automatically removing the prosthesis. The device comprises a head with a first plunger configured for being introduced in the compartment and moving the first plunger
(Continued)

in both directions to move the first plunger out when the spacer moves, causing removing the prosthesis, and when the first plunger moves in the opposite direction the head is extracted from the compartment. The attachment piece and bar for attaching the prosthesis respectively comprise a projection and a step to make it easier to remove the prosthesis.

8 Claims, 10 Drawing Sheets

(51) Int. Cl.
*A61C 13/08* (2006.01)
*A61C 3/00* (2006.01)
*A61C 3/16* (2006.01)

(52) U.S. Cl.
CPC .............. *A61C 13/26* (2013.01); *A61C 3/16* (2013.01); *A61C 3/164* (2013.01)

(58) Field of Classification Search
CPC ... A61C 8/0062; A61C 8/0083; A61C 8/0075; A61C 5/007; A61C 5/70; A61C 5/30; A61C 13/225; A61C 13/2255; A61C 13/26; A61C 13/265; A61C 13/2653; A61C 13/2656; A61C 13/273; A61C 13/275; A61C 13/267; A61C 13/2673; A61C 13/01; A61C 13/10; A61C 13/1016; A61C 13/1013; A61C 13/102; A61C 2013/2753; A61C 2013/2756
See application file for complete search history.

(56) References Cited

U.S. PATENT DOCUMENTS

| | | | | |
|---|---|---|---|---|
| 3,413,722 A | * | 12/1968 | Skinner | A61C 13/0003 433/169 |
| RE29,070 E | * | 12/1976 | Mays | A61C 13/273 433/172 |
| 4,931,016 A | * | 6/1990 | Sillard | A61C 8/0048 433/167 |
| 5,057,017 A | * | 10/1991 | Sillard | A61C 8/0048 433/167 |
| 5,678,996 A | * | 10/1997 | Dawson | A61C 13/2653 433/177 |
| 5,803,735 A | | 9/1998 | Gittleman | |
| 6,821,122 B1 | * | 11/2004 | Wintermantel | A61C 13/277 433/177 |
| 2012/0009542 A1 | | 1/2012 | Keddington et al. | |

OTHER PUBLICATIONS

International Search Report of PCT/ES2016/070378, dated Jul. 15, 2016.

* cited by examiner

IMPLANT-SUPPORTED DENTAL PROSTHESIS, REMOVAL DEVICE FOR AUTOMATICALLY REMOVING THE PROSTHESIS, ATTACHMENT PIECE FOR ATTACHING THE PROSTHESIS TO IMPLANTS AND IMPLANT SPLINTING BAR FOR ATTACHING THE PROSTHESIS TO IMPLANTS

CROSS REFERENCE TO RELATED APPLICATIONS

This application is the National Stage of PCT/ES2016/070378 filed on May 19, 2016, which claims priority under 35 U.S.C. § 119 of Spanish Application No. P201530692 filed on May 20, 2015, the disclosures of which are incorporated by reference. The international application under PCT article 21(2) was not published in English.

TECHNICAL FIELD

The present invention relates to an implant-supported dental prosthesis, to a removal device for easily and automatically removing the implant-supported prosthesis, to an attachment piece for attaching the prosthesis to implants, and to an implant splinting bar for attaching the prosthesis to implants, such that they all allow automatically removing the prosthesis by means of said removal device. The invention is comprised in the field of the oral rehabilitation in oral implantology and the field of dental prosthesis.

PRIOR ART

Dental prostheses of the prior art, the attachment of which to the patient's mouth is based on any type of dental implant, are referred to as implant-supported prostheses and have the advantage of offering a stronger attachment to the patient's mouth compared to other prostheses on the market. In turn, however, this strong attachment becomes a drawback when extracting the prosthesis from the mouth in order to clean it, which must be done after each meal or at least once a day.

To fix the prosthesis to dental implants which are fixed in the patient's mouth, prostheses have intermediate pieces made of a flexible material. This flexibility allows anchoring and extracting prostheses on implants. There are different degrees of hardness for these intermediate pieces, such that the dentist must select a combination of hardnesses for each of the intermediate pieces of the prosthesis such that it provides a stronger attachment but which at the same time allows extracting the prosthesis. Finding that balance between a firm attachment and extraction by the actual patient leads to a significant number of clinical check-ups and a great deal of discomfort for the patient, as well as having to change and restore the flexible intermediate pieces, all of which results in costs for the dental clinic and the patient. This problem is worsened as the fixing points increase and in people with little physical strength, in unskilled people or in people who depend on a caregiver.

The removal of said prostheses is performed today by trying to separate it from its housing starting from one end with expertise and by exerting enough strength using the fingers until they gradually separate the points of attachment, which as mentioned is very difficult or impossible in many cases. There is no instrument or device especially designed for removing implant-supported prosthesis. The instruments that do exist have been created for conventional prostheses or dentures. They are very basic and rigid one-piece instruments in the form of a "hook" or "bent clamp" made for the purpose of being gripping any "nook" or "projection" offered by the prosthesis or artificial denture. The risk of using these instruments is very high because any "slip-up" or "slip" when applying force can cause tearing, injuries, contusions, fractures, etc., on the user's oral-dental structures, even when these instruments are used by qualified professionals.

The invention allows removing the prosthesis automatically by inserting a head of a new device into one side of the prosthesis and pushing a button. The separation strength provided is far superior to that which can be done with the hands and is preferably located contiguous to the first point of attachment of the prosthesis so that when this point of attachment is separated, the remaining points of attachment can continue to be separated one after another.

The device allows extracting the dental prosthesis safely, quickly and automatically, eliminating the risks of injury present in the methods existing up until now, i.e., or is, manually or with rudimentary instruments. In turn, it allows using harder, intermediate, flexible retaining pieces from the first placement of the prosthesis in a dental clinical, offering the best results to the patient from the start and preventing repeated visits to the clinical to find the balance between the firm attachment and manual extraction.

DISCLOSURE OF THE INVENTION

To achieve the objectives and solve the drawbacks discussed above, avoiding the serious difficulties which most users of implant-supported prostheses of this type encounter when they are removed, the present invention allows removing the prosthesis automatically for which it provides a new prosthesis, a new removal device for removing the prosthesis, a new attachment piece for attaching the prosthesis to the implant and a new implant splinting bar for attaching prostheses to implants, assuring reliability, simplicity and ease of use for the person using the implant-supported prosthesis or their caregiver.

As mentioned, implant-supported prostheses comprise intermediate pieces for fixing them to the implants which have previously been arranged in a user's gum. The main novelty of the prosthesis of the invention consists of the fact that it comprises at least one compartment housed inside the prosthesis and provided with a side opening which is arranged in correspondence with an opening of the prosthesis such that the compartment is communicated with the outside of the prosthesis. Furthermore, the prosthesis comprises a spacing member which is included inside the compartment, which can be actuated through the side opening and is arranged proximal to an implant. This entire configuration allows causing the movement of the spacing member when the spacing member is actuated by means of a tool, pressing against the implant, such that it causes the separation of the prosthesis from said implant.

In the preferred embodiment of the invention, the spacing member comprises two arms articulated on a shaft like pincers, and at least one of said arms is provided, in one of its end areas, with a cavity facing the other arm and the side opening. Furthermore, the end of the upper arm, opposite the one with the cavity, is located near an implant to cause the arms to open when the tool is introduced in the cavity, which causes the separation of the prosthesis from the implant, such that it is removed automatically.

The spacing member is fixed in an articulated manner inside the compartment, such that when the arms open, only the upper arm located near the implant at the end opposite the one with the cavity moves. To aid in the removal, the end of the upper arm arranged proximal to the implant comprises a step on which said implant is supported.

Furthermore, in the preferred embodiment the compartment comprises a flare in which the side opening is included so as to allow opening the ends of both arms in which the cavity is included.

The invention envisages that the side opening of the compartment includes a plug member to prevent pieces of food from entering the compartment. This plug member can be a flexible membrane covering the inlet opening and moving when the tool is introduced.

In the preferred embodiment, it is envisaged that both arms comprise respective cavities with a configuration extending transversely towards the rear portion of the prosthesis and complementary to the portion of the tool which is introduced in the cavity, such that this configuration makes it considerably easier to open the spacing member when said tool is introduced in the side opening of the compartment.

Furthermore, the invention relates to a device which allows automatically removing the prosthesis described above, characterized in that it comprises a head which is provided with a first plunger, both being configured so as to allow the introduction thereof in the compartment through its side opening and the side opening of the prosthesis. The device also comprises means for moving the first plunger in both directions, such that by means of this configuration when the head is introduced in the opening of the compartment, it allows the movement of the first plunger out of the head to cause the movement of the spacing member, which leads to removing the prosthesis. Likewise, when the first plunger moves in the opposite direction the head can be extracted from the compartment, being ready to remove another prosthesis.

The front end of the first plunger includes a punch provided for being introduced in the cavity of the spacing member of the prosthesis.

Furthermore, the first plunger comprises an inclined flare on which an expandable member complementary to the first plunger is coupled, such that when the outward movement of the first plunger occurs, it causes the radial expansion of the expandable member and anchoring thereof in the compartment, so the head is fixed in the compartment such that the movement of the first plunger allows introducing the punch in the cavity of the spacing member without the user having to exert any effort since the head is fixed to the compartment.

The invention envisages that the expandable member is aided by a coil spring which is retained by means of a ring and an annular cover in the head to keep the expandable member in constant contact with the first plunger. The expandable member comprises a perimetral lip abutting with the inner wall of the compartment when the first plunger moves out of the head to achieve a solid fixing of the head to the inside of the compartment, preventing the first plunger from being able to come out of the compartment when the first plunger is introduced in the cavity of the spacing member.

In order to allow movement of the plunger in both directions, the head comprises a chamber in which the first plunger is arranged, the rear portion of which communicates with a hydraulic circuit controlling the movement of the first plunger in both directions.

The head is arranged in a handle in which the hydraulic circuit is included which is provided with an electric motor, with reduction gear and built-in anti-interference electronic circuit, causing the angular movement in both directions of a threaded bushing screwed on a threaded screw fixed in the handle. The bushing and threaded screw are provided with a conduit comprising a second plunger and communicated with the rear portion of the chamber to cause the longitudinal movement of the second plunger in both directions when the motor is activated by means of an electronic circuit through a switch and both being powered by batteries.

Furthermore, the head is attached to a flexible neck provided with a conduit communicating the rear portion of the chamber of the first plunger with the conduit of the threaded screw, so as to allow introducing the head in the side opening of the prosthesis without introducing the fingers in the patient's mouth. The neck is fixed to the handle and it is envisaged that the fixing is detachable to make it easier to repair the device. The invention envisages that all the members of the device are detachable to make it easier to repair it.

In one embodiment of the invention, the device comprises a casing including the hydraulic circuit which is attached to the conduit of the neck communicated with the rear portion of the chamber through an extending tube. In this case, the hydraulic circuit comprises a motor with a reduction gear moving a hydraulic pump with a reservoir for the hydraulic fluid and the entire assembly is controlled by an electronic circuit and powered by batteries to control operation of the motor. The casing comprises fixing means for being fixed to an object, such that it can be located on any member and the arrangement of the head in the prosthesis for the removal thereof is allowed by means of the extender. As examples, the casing can hang on the user's body, be on a shelf, a table, a wheelchair, or a seat back.

As described, the spacing member of the compartment is arranged proximal to an implant so that the spacing member moves when actuated, pressing against a projection of a new attachment piece for attaching the prosthesis to implants or a new implant splinting bar for attaching the prosthesis to implants, causing the separation of the prosthesis from said implant. In bar splinted implant attachment system, the new end of the bar included in the invention is what comes into contact with the step of the spacing member. In independent non-splinted attachment systems, i.e., without a bar, the prosthesis is fixed on a new add-on included in the invention which is located in the implant and to which it is fixed by means of a through screw. The add-on includes a new projection located proximal to the compartment and on which the step of the spacing member is supported in order to lift the prosthesis. The new add-on comprises an outer portion with a polygonal-shaped contour complementary to an inner polygonal-shaped portion of the implant, which is fixed to the user's jaw bone, so that the outer polygonal-shaped portion is housed in the inner polygonal-shaped portion of the implant in a selected position, preventing rotation when the implant is screwed in. The positions that can be chosen depend on the number of polygonal faces and they are fixed by means of the through screw. Accordingly, the add-on has the novelty of comprising a projection which is located proximal to the compartment before the add-on is fixed in the implant and is then fixed in this position by means of the through screw so that it can support the step of the spacing member in the projection.

The new implant splinting bar for attaching the prosthesis to implants comprises a step at the end thereof that is complementary to the step of the spacer, on which said step of the spacing member is supported and presses when said spacer is actuated.

DISCLOSURE OF THE PREFERRED EMBODIMENT

The invention relates to a prosthesis (g), to a removal device for removing the prosthesis, to a new piece for fixing the prosthesis to the implant for the case in which the prosthesis is fixed to the implant by means of a non-splinted implant attachment system, and to an implant splinting bar for attaching the prosthesis to implants for the case of attaching splinted implants.

The prosthesis (g) comprises a preferably metallic compartment (1) which is provided with a side opening (1a) arranged in correspondence with a side opening (28) of the prosthesis (g). The compartment (1) includes a spacing member (2), which is also preferably metallic, which in the embodiment is formed by two arms (2a) articulated on a shaft (2b), one side of the arms (2a) near the end thereof having a cavity (2c) facing the side opening (1a) of the compartment (1), all this being like small pincers, such that if a first plunger (3) is introduced in the cavity (2c), the pincers open, the ends thereof being separated from one another. In the embodiment, the end which is arranged at the back of the compartment (1) and opposite the end including the cavity (2c) is fixed to said compartment (1) by means of a pin (2e) with rotational possibility, and at this same end of the other arm there is comprised a step (2d) on which an implant is supported, as will be described below, preferably an implant end.

Figure 5:
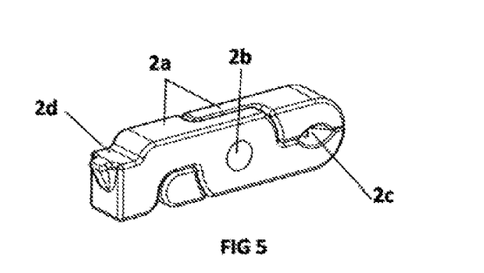
FIG. 5 shows a perspective view of an embodiment of the opening member, which is included in the compartment of the prosthesis, in the closed position, the opening of which by means of the head of the device causes removing the prosthesis.
Figure 6:
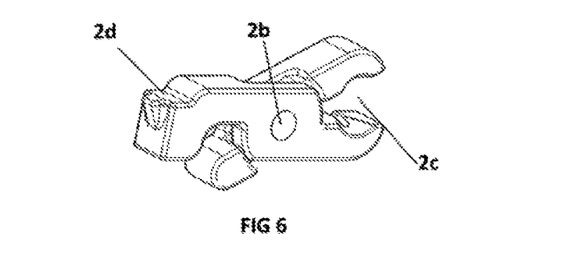
FIG. 6 show a view equivalent to the preceding figure in which the opening member is open for removing the prosthesis.
Figure 7:
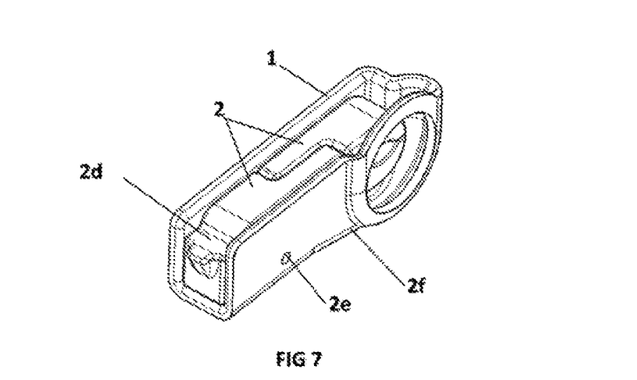
FIG. 7 shows a perspective view of the compartment with the opening member mounted therein, which are housed inside the prosthesis.
Figure 8:
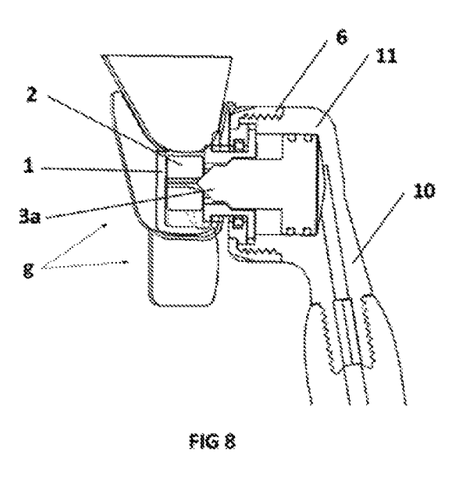
FIG. 8 shows a sectioned view of the head of the device introduced in the compartment before the removal.

Furthermore, the compartment has a side flare (2f) in which the opening (1a) is included, such that when a first plunger is introduced in the cavity (2c), the ends of the arms (2a) including the cavity (2c) open and at the opposite ends of which only the upper end which is proximal to or in contact with the implant opens, the entire movement for opening the arms (2a) being applied to said end, causing the separation of the prosthesis (g) from the implant.

Figure 12:
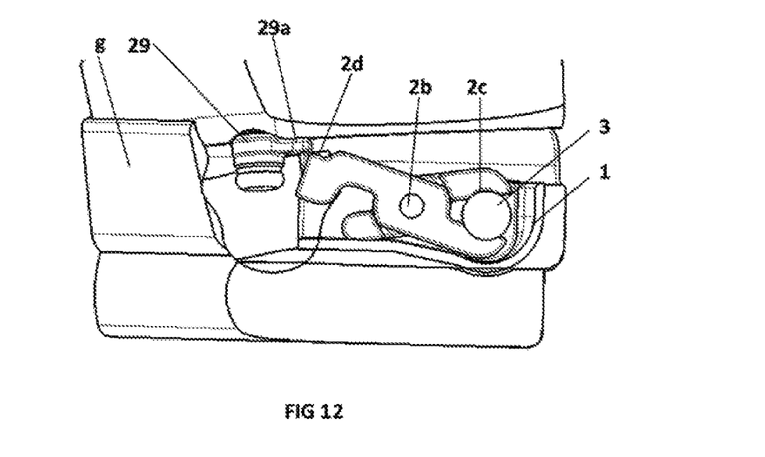
FIG. 12 shows another sectioned view of what is depicted in FIG. 10 at the time in which the prosthesis is removed.
Figure 13:
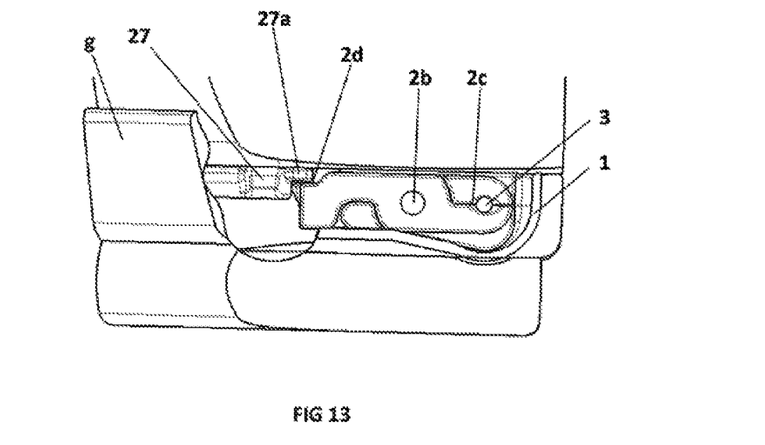
FIG. 13 shows a view equivalent to FIG. 12 for the case in which the prosthesis is attached by means of the new splinting bar, showing the arrangement of the step of the spacing member on the new bar in the initial moment of the opening so as to allow removing the prosthesis.

In bar splinted implant attachment systems including a bar (27) (FIG. 12), it is the actual end (27a) of the bar (27) that comes into contact with the step (2d), where said end (27a) is a stepping complementary to step (2d) and in independent, non-splinted attachment systems, i.e., without a bar, in which the prosthesis is fixed on an add-on (29) (FIGS. 10, 11a-11c and 12) located in the implant (30) and to which it is fixed by means of a through screw (31), there is a projection (29a) provided in the add-on (29) located proximal to the compartment (1) and on which the step (2d) is supported for lifting the prosthesis (g).

Therefore, the invention provides a new bar (27) for splinted implant attachment according to the description made and it also provides a new attachment piece for attaching the prosthesis (g) to the implant (30) in non-splinted attachment systems, which in this case is formed by a new add-on (29) the novelty of which resides in the incorporation of the projection (29a) so as to allow removing the prosthesis by means of the spacer (2) like pincers, as described. To assure the position of the projection (29a) in the suitable position, the add-on (29), as is conventionally envisaged, has an outer portion (29b) with a polygonal-shaped contour complementary to an inner polygonal-shaped portion (30a) of the implant such that the outer polygonal-shaped portion (29b) is housed in the inner polygonal-shaped portion (30a) of the implant (30) in the position in which the projection (29a) is located proximal to the compartment (1), and then it is fixed in this position by means of the through screw (31) so that the step (2d) is supported on the projection (29a). The invention envisages that the side opening (1a) can be covered by a membrane made of a flexible material (not depicted) to reduce the entry of food into the compartment (1).

The compartment (1) and spacer (2) assembly could be mounted on new prostheses (g) during the resin muffling process inside the mold inserted in prostheses or in already existing prostheses by means of milling a housing and opening (28) allowing the mounting thereof.

Figure 14:
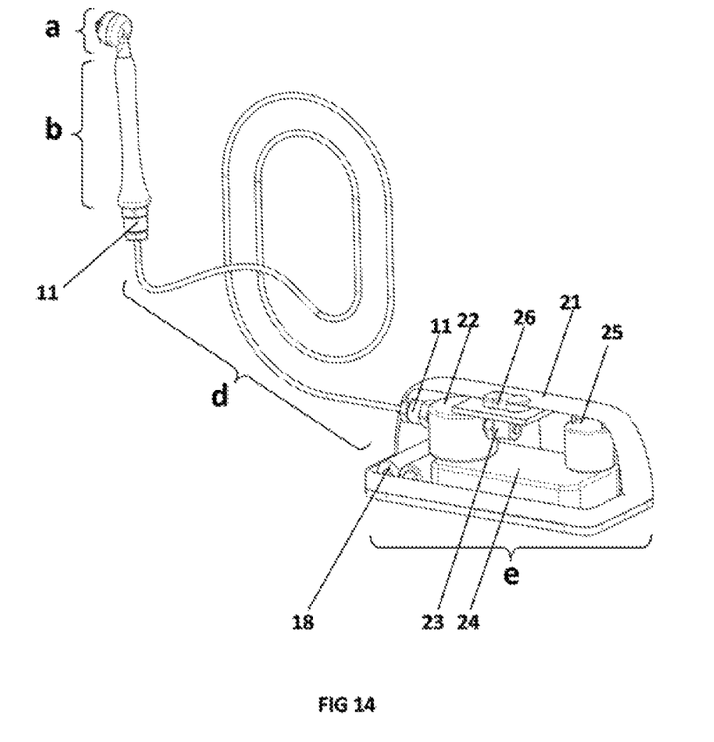
FIG. 14 shows a view of another possible embodiment of the device of the invention in which the first plunger is actuated by means of a hydraulic pump controlled by a circuit of control.

The removal device comprises a head (a), neck (b) and handle (c) (for one embodiment of the invention (FIGS. 1 and 2), and for another embodiment it comprises the head (a), neck (b), extending tube (d) and control box (e), (FIG. 14).

The head (a) is formed by preferably metallic components comprising a first plunger (3) provided at the front end thereof with a punch (3a), and provided with an inclined flare (3b) in which preferably metallic expandable members (4) are coupled, such that they are in contact enveloping said first plunger (3), and they are kept in this position by means of the action of a coil spring (9) which is retained by means of a ring (5), and the entire assembly is fixed in the head (a) by means of a threaded cover (6). This configuration means that when the first plunger-punch (3-3a) moves forward, the expandable members (4) expand for the purpose of anchoring the device in the side opening (1a) of the compartment (1) by means of a perimetral lip (4a) provided in said expandable members, and when it moves backwards they close, returning to the initial position. The ring (5), the coil spring (9) and the threaded cover (6) keep the expandable members (4) in the correct position during movement of the first plunger (3). The first plunger (3) is arranged in a chamber (7) the rear portion of which communicates with a hydraulic oil conduit (8) which is injected or discharged in said rear portion of the chamber (7) to cause the forward and backward movement and of the first plunger-punch (3-3a). When the hydraulic oil is discharged, the first plunger-punch (3-3a) moves backward, during which movement the expandable members (4) close, and when filling occurs, the oil moves forward, opening the expandable members (4).

Figure 1:
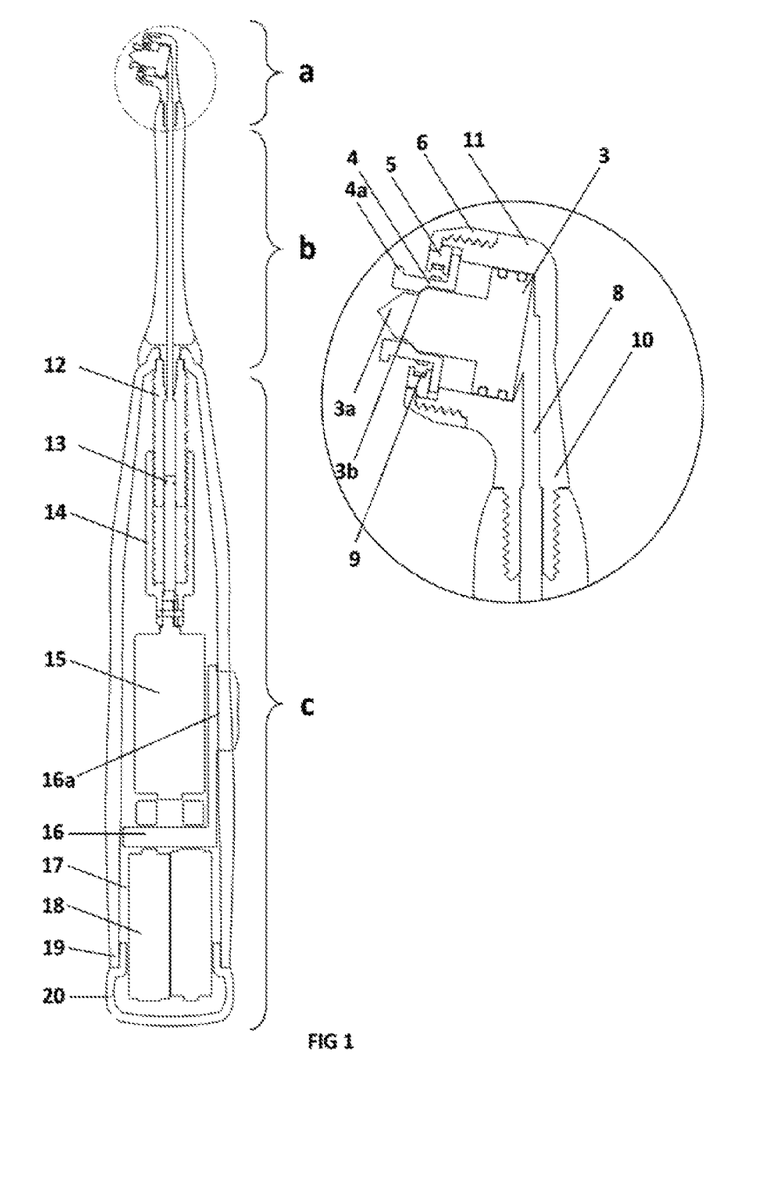
FIG. 1 shows a sectioned side view of the removal device of the invention in the position in which the first plunger of the head is in standby so as to allow the introduction thereof in the prosthesis. It also shows a detail of the head in this position.
Figure 2:
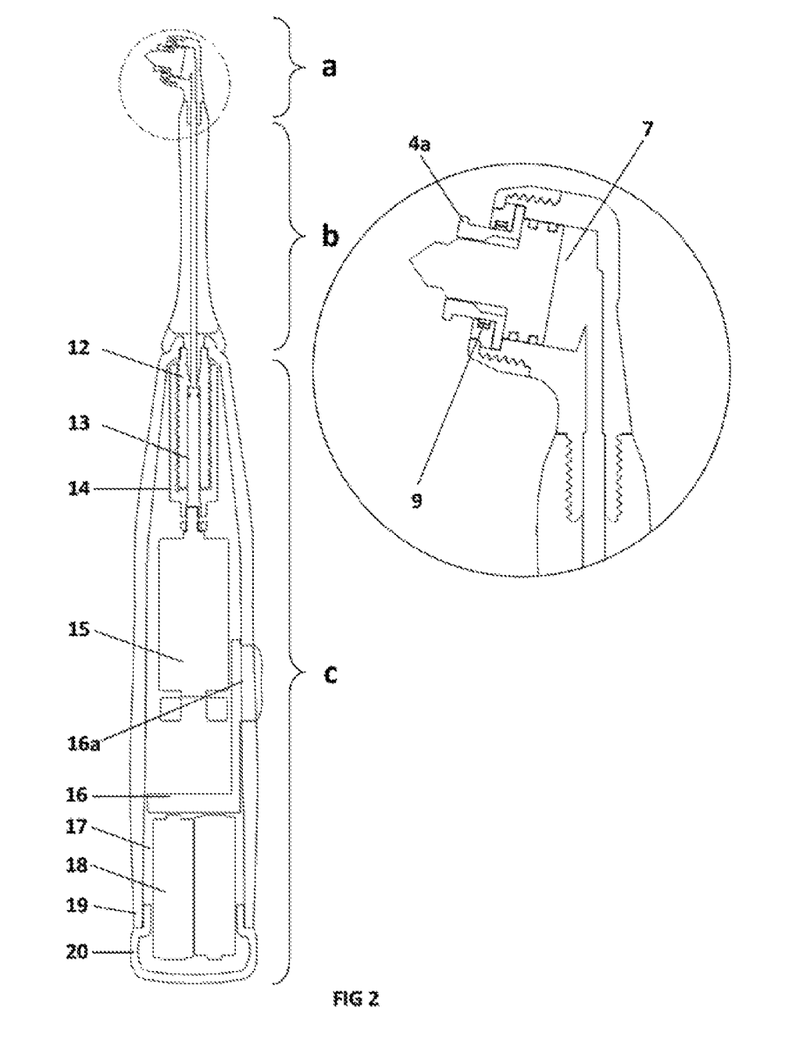
FIG. 2 shows a sectioned side view equivalent to the preceding figure of the removal device of the invention in the position in which the first plunger has been moved for removing a prosthesis. It furthermore shows a detail of the head in this position.
Figure 3:
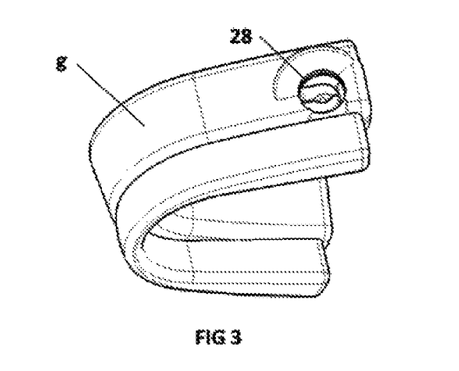
FIG. 3 shows a perspective view of a possible embodiment of the prosthesis of the invention.
Figure 4:
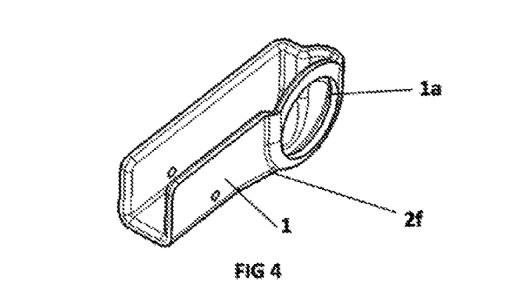
FIG. 4 shows a perspective view of the compartment which is included in the prosthesis in which the head of the device is introduced for removing said prosthesis.

The head (a) comprises an extension (10) with an end threaded on which the neck (b) of the device is screwed such that the head (a) can be dismounted.

The neck (b) is the piece joining the head (a) with the handle (c) and is essentially a tube through which the hydraulic oil runs, connecting with the conduit (8), and which can also include wires for a control function located close to the head (a). The neck (b) is long enough so as to allow the head (a) to be introduced in the side opening (1a) of the compartment (1) of the prosthesis (g) without difficulties and without having to introduce the fingers in the patient's mouth. Furthermore, the neck (b) is made of a flexible material to prevent the movements the user makes from causing excess stress on the head (a).

The handle (c) comprises a threaded screw (12) on which a threaded bushing (14) is screwed, internally comprising a conduit connecting with the conduit (8) through the tube constituting the neck (b) and comprising a second plunger (13), such that it acts as a cylindrical hydraulic chamber, the second plunger (13) of which moves together with the threaded bushing (14) which is rotated by an electric motor (15) with a reduction gear and a built-in anti-interference electronic circuit. The second plunger (13) does not move integrally with the threaded bushing (14) internally, but rather rotates internally and will only move longitudinally in the conduit of the threaded screw (12) and threaded bushing (14) to prevent friction and lateral wear. The rotation of the motor (15) screws on or unscrews the threaded bushing (14) with respect to the threaded screw (12), moving the second plunger (13), causing the injection or suction of the hydraulic oil, which in turn causes the movement of the first plunger (3) of the head (b).

Furthermore, the handle (c) internally includes an electronic circuit (16) with a switch (16a) and batteries (18) of any type, such as contact or induction rechargeable batteries or any energy accumulator rotating the motor (15). All this is encapsulated in a casing (19) and hermetically sealed with a cover (20).

FIG. 14 shows another embodiment of the invention in which the handle (c) of the device has been replaced with a casing (e), which in the embodiment is a box (21) comprising a mini hydraulic pump (22) that has to contain pressure without any leaks, therefore a suitable one would be a gear pump, but a peristaltic pump or another type of pump that may appear on the market in the future could also be used. The pump (22) incorporates a small oil reservoir (23) through which the oil that is discharged from the head during the suction process passes. The pump (22) is rotated by a reduction gear (24) with a motor (25). It furthermore includes an electronic circuit (26) which controls the opening, closing and ends of stroke or excess pressure (for example by means of controlling the operating amperage of the motor) and includes the corresponding batteries (18) of any type, for rotating the motor and feeding the electric circuit.

The outlet of the pump (22) is connected to an extending tube (d) which, by means of a connector (11), is connected with the neck (b) for injecting-suctioning the oil in the rear portion of the chamber (7) of the head (a), achieving the aforementioned functionality. The extending tube (d) is flexible in order to be able to freely manipulate the head and allows the box (21), during use, to be located on a table, anchored to a belt, a pocket, a wheelchair, etc. The connector (11) used is a conventional connector for pressures not exceeding 8 bar.

In the case of the embodiment of FIGS. 1 to 13, it is easily understood that in order to extract a prosthesis (g), the first plunger (3) of the head (a) is introduced in the side opening (1a) and then the switch (16a) is operated, such that the electronic circuit (16) activates the motor (15) screwing the threaded bushing (14) on the threaded screw (12), moving the second plunger (13) which initiates the injection of hydraulic oil towards the head (a), which causes the first plunger-punch (3-3a) to move outwards, opening the metallic expandable members (4) that are anchored in the side opening (1a) by the arrangement of the perimetral lip (4a) abutting with the inner walls of the side opening (1a).

The first plunger-punch (3-3a) continues entering and presses into the cavities (2c) at one end of the spacing member (2), which forces the spacers (2) to open by sliding. More specifically, the punch (3a) is introduced in the cavities (2c) of the arms (2a) such that they open, which determines the separation of the prosthesis from the implant, by pressing the end of the spacer (2), more specifically the step (2d) thereof, against the implant, which can be the end (27a) of the bar (27) or the projection (29a) as described, depending on the used attachment system, so when this point of attachment is separated, the remaining points of attachment continue to be separated one after another. The separation strength it provides is far superior to that which can be provided using the hands.

To make it easier to open the arms (2b), the cavities (2c) have a configuration extending transversely towards the rear portion of the prosthesis and complementary to that of the punch (3a), to make it easier to open the arms (2b) of the spacing member (2) when the punch (3a) is introduced in the side opening (1a) of the compartment (1).

Figure 9:
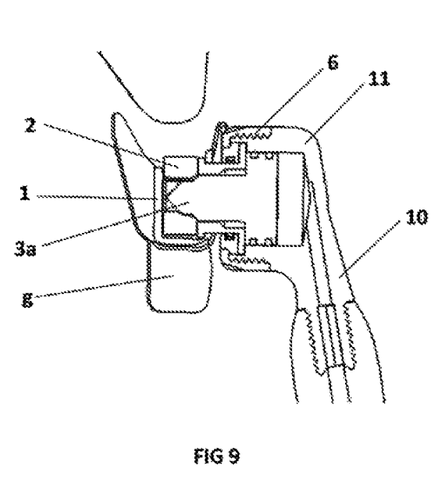
FIG. 9 shows a view equivalent to the preceding figure in which the first plunger of the head has been actuated, removing the implant.
Figure 10:
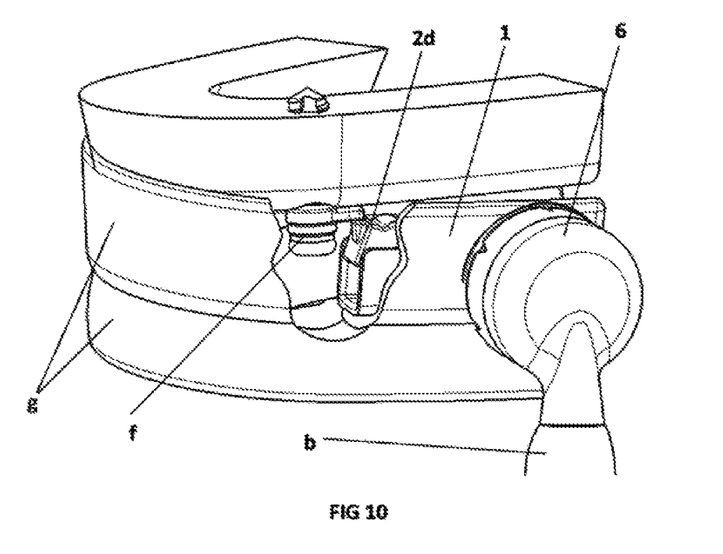
FIG. 10 shows a partially sectioned perspective view in which the first plunger has been actuated as depicted in FIG. 9, removing the prosthesis, for the case in which a new attachment piece for attaching the prosthesis to implants as depicted in FIGS. 11a-11c is used.
Figure 11A:
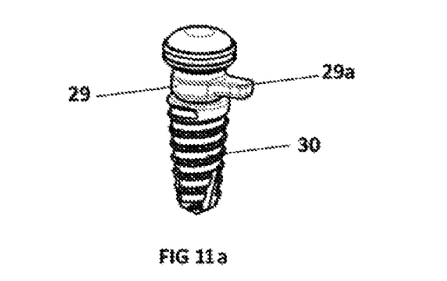
FIGS. 11a-11c show different views of the new piece for fixing the prosthesis to the implant in independent, non-splinted implant attachment systems, i.e., without a bar, so as to allow removing the prosthesis.
Figure 11B:
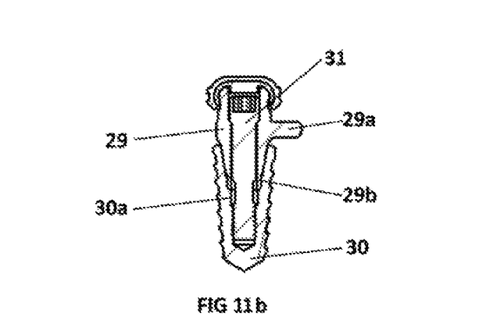
Figure 11C:
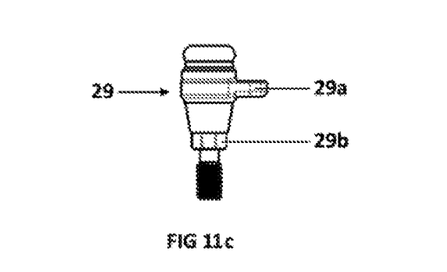

The prosthesis (g) moves with the arms (2b) of the spacer (2) due to contact between metallic surfaces, causing extraction of the prosthesis (g).

From the start of the forward movement of the first plunger (3), the expandable members (4) remain anchored by the perimetral lip (4a), so that the punch (3a) can exert pressure and the prosthesis (g) remains attached to the head (a) once extracted.

When the switch (16a) is operated again, the first plunger-punch (3-3a) moves back and the expandable members (4) close, allowing the user to place the prosthesis (g) in the desired location, even without touching it.

For the case of the embodiment of FIG. 14, the operation is the same as what has been described, with the difference that the movement of the first plunger (3) is made by the hydraulic circuit included in the casing (e) that has been described.

If required, it is envisaged that the prosthesis (g) can comprise the compartment (1) at the two ends for fixing the prosthesis, or at any other point required for extraction.

To manufacture the metallic members it is necessary to use very strong materials such as stainless steel with surface treatments or titanium, manufacturing them by means of high-precision milling and turning and casting. Plastic pieces manufactured by injection molding are also used. Advanced bi-material injection and plastic injection techniques are used to achieve different surface finishes and flexibility in some areas.

The invention claimed is:

1. An implant-supported dental prosthesis, comprising intermediate pieces for fixing the prosthesis (g) to implants arranged in the gum of a user, wherein the dental prosthesis at least comprises:
- a compartment (1) housed inside the prosthesis and provided with a side opening (1a) arranged in correspondence with an opening (28) of the prosthesis (g) for communicating the compartment (1) with the outside of the prosthesis,
- a spacing member (2) included in the compartment (1) that can be actuated through the side opening (1a) and arranged proximal to an implant, that comprises two arms (2a) articulated on a shaft (2b), where the spacing member (2) moves when it is actuated by a tool pressing the spacing member against the implant causing the separation of the prosthesis (g) from said implant.

2. The implant-supported dental prosthesis according to claim 1 wherein at least one of the two arms (2a) of the spacing member (2) has an end area with a cavity (2c) facing the other arm and the side opening (1a); where an end of an upper one of the arms, opposite the arm with the cavity (2c) is located near the implant to cause the arms (2) to open and the prosthesis (g) to separate from the implant when the tool is introduced in the cavity (2c).

3. The implant-supported dental prosthesis according to claim 2, wherein the spacing member (2) is fixed in an articulated manner inside the compartment (1), such that when the arms (2) open, only the upper arm located near the implant at the end opposite the arm with the cavity (2c) moves.

4. The implant-supported dental prosthesis according to claim 3, wherein the end of the upper arm arranged proximal to the implant comprises a step (2d) on which said implant is supported.

5. The implant-supported dental prosthesis according to claim 3, wherein the compartment comprises a flare (2f) in which the side opening (1a) is included so as to allow opening the ends of both arms (2a) in which the cavity (2c) is included.

6. The implant-supported dental prosthesis according to claim 1, wherein the side opening (1a) of the compartment (1) comprises a plug member to prevent pieces of food from entering the compartment.

7. The implant-supported dental prosthesis according to claim 6, wherein the plug member is a flexible membrane covering the inlet opening and moving when the tool is introduced.

8. The implant-supported dental prosthesis according to claim 2, wherein both arms (2a) comprise respective cavities (2c) with a configuration extending transversely towards a rear portion of the prosthesis and which is complementary to the configuration of the tool to facilitate opening the spacing member (2) when said tool is introduced in the side opening (1a) of the compartment (1).

* * * * *